US00PP24602P3

(12) United States Plant Patent
Egger

(10) Patent No.: US PP24,602 P3
(45) Date of Patent: Jul. 1, 2014

(54) ***SEDUM* PLANT NAMED 'CHERRY TRUFFLE'**

(50) Latin Name: *Sedum telephium*
Varietal Denomination: Cherry Truffle

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 93 days.

(21) Appl. No.: 13/573,504

(22) Filed: Sep. 19, 2012

(65) Prior Publication Data

US 2014/0082806 P1 Mar. 20, 2014

(51) Int. Cl.
*A01H 5/00* (2006.01)

(52) U.S. Cl.
USPC ..... Plt./479

(58) Field of Classification Search
USPC ..... Plt./263.1, 479
See application file for complete search history.

*Primary Examiner* — Susan McCormick Ewoldt
(74) *Attorney, Agent, or Firm* — Klarquist Sparkman, LLP

(57) ABSTRACT

A new and distinct hybrid of *Sedum* plant substantially as shown and described characterized by pink flowers in large inflorescences, purple black leaves in summer with cut leaf margins, two-toned olive and purple leaves in the spring, strongly upright stems, and a medium, clumping habit.

1 Drawing Sheet

Botanical denomination: *Sedum telephium.*
Variety designation: 'Cherry Truffle'.

BACKGROUND OF THE INVENTION

The present invention relates to a new and distinct cultivar of *Sedum* and given the cultivar name of 'Cherry Truffle'. *Sedum* is in the family Crassulaceae. *Sedum* 'Cherry Truffle' originated from a planned cross between an unnamed proprietary, unpatented *Sedum telephium* seedling and *Sedum telephium* PP5, another proprietary, unpatented plant. The new cultivar is planned as an accent for the landscape that is of medium height with strong stems that won't fall over.

Compared to *Sedum telephium* PP5, the new cultivar is larger with a better crown and with a larger inflorescence.

Compared to *Sedum* 'Raspberry Truffle' (U.S. Plant Pat. No. 22,755), the new variety is larger with a broader habit that more quickly forms multiple crowns and with leaves that are purple black rather than purple brown.

This new and unique *Sedum* is distinguished by:

1. pink flowers in large inflorescences,
2. purple black leaves in summer with cut leaf margins,
3. two-toned olive and purple leaves in the spring,
4. strongly upright stems,
5. and a medium, clumping habit.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a three-year-old *Sedum* 'Cherry Truffle' in flower growing in full sun in the trial bed outside in August in Canby, Oreg.

FIG. 2 shows a close up of the same plant in the spring.

DETAILED PLANT DESCRIPTION

The following is a detailed description of the new *Sedum* hybrid based on observations of two-year-old specimens grown in a the trial bed in full sun under typical outdoor conditions in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on *The Royal Horticultural Society Colour Chart, 5th* edition.

Plant:
- *Type.*—Herbaceous perennial.
- *Hardiness.*—USDA Zone 4 to 9.
- *Size.*—50 cm tall from the ground to the base of the inflorescence and 54 cm wide.
- *Habit.*—Erect, clumping.
- *Vigor.*—Excellent.

Stem:
- *Number.*—About 15.
- *Size.*—40 cm long and 11 mm wide.
- *Color.*—Greyed Purple 187A.
- *Surface.*—Glabrous.

Leaf:
- *Type.*—Simple.
- *Arrangement.*—Variable.
- *Shape.*—Ovate.
- *Apex.*—Acute.
- *Base.*—Cuneate.
- *Venation.*—Pinnate.
- *Margins.*—Irregularly serrate.

*Blade size*.—Grows to 7.5 cm long and 4.5 cm wide.
*Surface*.—Glabrous.
*Petiole*.—Leaves sessile.
*Leaf color*.—Summer and early fall leaves topside closest to Greyed Purple N187B, including the veins, bottom side closest to Greyed Purple N187B except where shaded closest to Greyed Green 191A, veins Greyed Purple N186C; spring topside Greyed Purple N187A shading to Greyed Green 191B on the bottom half, bottom side Greyed Green 191B heavily tinted Greyed Purple N187A, with the main vein Greyed Brown 199D on top and bottom side.

Inflorescence:
*Type*.—Terminal, corymbose, umbel-like.
*Number of flowers*.—About 1000 per stem.
*Peduncle*.—8 to 10 cm tall and grows to 6 mm wide, Greyed Purple 187A, succulent, glabrous.
*Size*.—Grows to 14 cm deep and 18 cm wide.
*Bloom period*.—August through September in Canby, Oreg.

Flower bud:
*Size*.—2.5 mm wide, 4 mm deep.
*Description*.—Ovoid.
*Color*.—Red Purple 59A on top half and lightening to Red Purple 62D on bottom.

Flower:
*Type*.—Complete, actinomorphic.
*Shape*.—Stellate.
*Size*.—6 mm deep and 11 mm wide.
*Color*.—Purple 76D.
*Corolla description*.—4 mm deep and 5 mm wide, 5 petals, each lanceolate, 3 mm long and 1.2 mm wide, margins entire, tip acuminate, both sides glabrous and Red Purple 59A on top half and lightening to Red Purple 62C on bottom.
*Calyx description*.—1.5 mm deep and 1.5 mm wide, campanulate, 5 lobes, divided to the base, margins entire, tip acute, glabrous, Grey Brown N 199B on both sides.
*Stamen description*.—10 in number, 3 mm long, filaments 3 mm long, Red Purple 62D, anthers Yellow Orange 19A, no pollen, male sterile.
*Pistil description*.—5 separate prominent carpels, each 3 mm deep and 1 mm wide, Red Purple 59A on top half to Red Purple 62D on bottom half.
*Fragrance*.—None.
*Lastingness*.—Each stem lasts up to a month.

Fruit:
*Type*.—Ventrally dehiscent follicle, erect, attenuate.
*Fertility*.—None.
*Color*.—Brown 200A.

Seed: No seed produced.

Disease and pest tolerance: The new cultivar is typical to the genus. No known resistances to pests or diseases. No problems have been found in Canby, Oreg.

I claim:

1. A new and distinct hybrid of *Sedum* plant as herein illustrated and described.

* * * * *

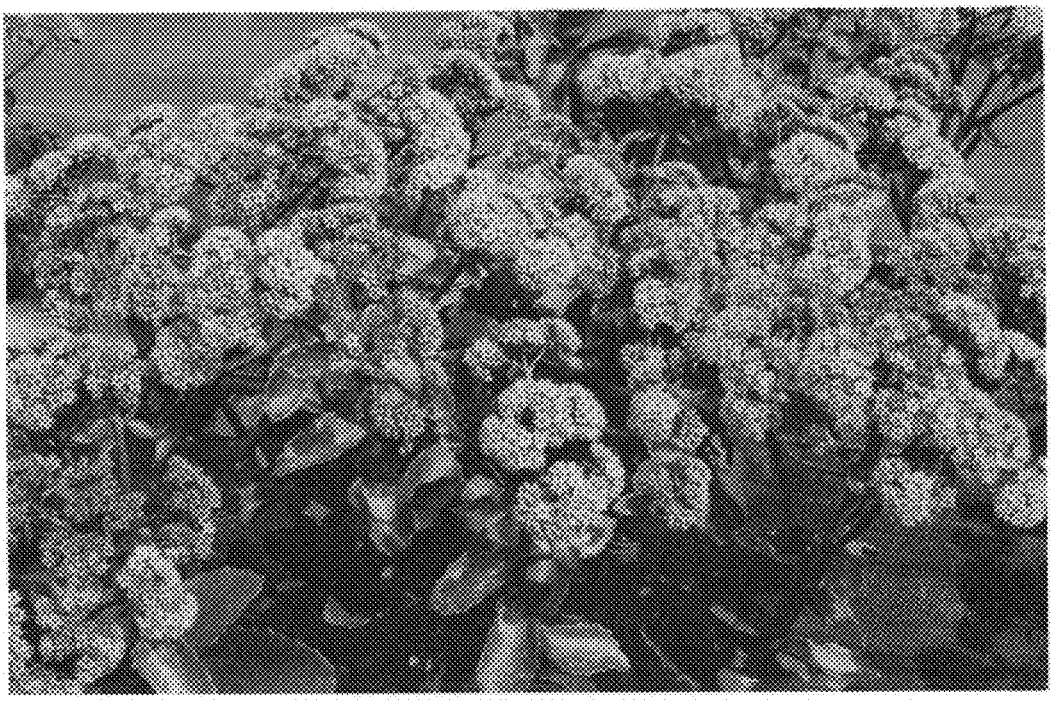
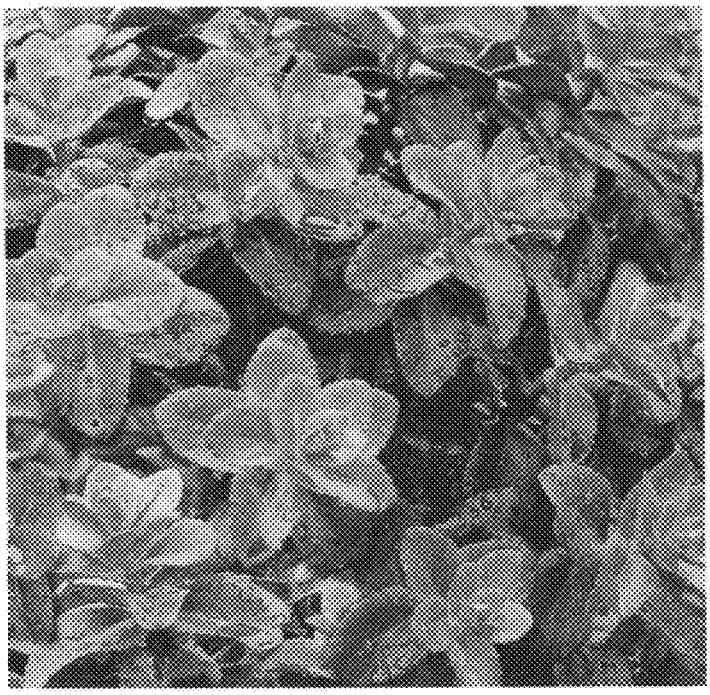
FIG. 1 above,
FIG. 2 on left